United States Patent [19]

Sturm

[11] 4,133,954
[45] Jan. 9, 1979

[54] PYRROLO- AND PYRIDO-1,4-BENZOXAZIN-3-(2H)-ONE DERIVATIVES AS MICROBICIDES

[75] Inventor: Elmar Sturm, Aesch, Switzerland

[73] Assignee: Ciba-Geigy Corporation, Ardsley, N.Y.

[21] Appl. No.: 850,445

[22] Filed: Nov. 10, 1977

[30] Foreign Application Priority Data

Nov. 16, 1976 [CH] Switzerland .................. 14404/76

[51] Int. Cl.² ......................................... C07D 498/04
[52] U.S. Cl. ............................. 544/101; 424/248.54
[58] Field of Search ......................................... 544/101

[56] References Cited

U.S. PATENT DOCUMENTS 3,883,522  5/1975  Gerster ............................... 544/101

FOREIGN PATENT DOCUMENTS 2505474  8/1975  Fed. Rep. of Germany .......... 544/101

OTHER PUBLICATIONS

Techer et al. "C. R. Acad. Sc. Paris" (1969) vol. 269, pp. 564-566.
Nagarajan et al. "Tetrahedron" vol. 29, pp. 2571-2573 (1973).
Nagarajan et al. "Chem. Abstracts" vol. 82 (1975) No. 118772z.

Primary Examiner—Henry R. Jiles
Assistant Examiner—R. W. Ramsuer
Attorney, Agent, or Firm—Harry Falber

[57] ABSTRACT

Compounds of the formula I

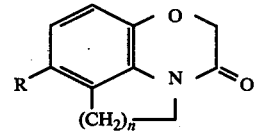

wherein
R represents hydrogen, methyl or ethyl and
n represents the number 1 or 2 are effective in combatting microbicides.

3 Claims, No Drawings

PYRROLO- AND PYRIDO-1,4-BENZOXAZIN-3-(2H)-ONE DERIVATIVES AS MICROBICIDES

The present invention concerns microbicidal compositions containing, as at least one active ingredient a compound having the formula I

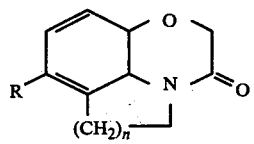 (I)

wherein

R represents hydrogen, methyl or ethyl and n represents the number 1 or 2.

Compounds wherein n represents 1 are known for example as 5,6-dihydro-pyrrolo [1.2.3-de]-1.4-benzoxazin-3(2H)-ones.

Compounds wherein n represents 2 are known for example as 5H-pyrido-6,7-dihydro[1.2.3-de]-1.4-benzoxazin-3(2H) ones. 5H-pyrido-6,7-dihydro[1.2.3-de]-1.4-benzoxazin-3-(2H)-one [R=H; n = 2] is known from C.R. Acad. Sc. Paris, Serie C, pp 564–6 [1969]. This article describes a process for preparing this compound comprising Michael-addition of 2,3-dihydro-3-oxo-benzoxazin (1.4) to e.g. acrylic acid ester with subsequent saponification of the ester and ring-closure with polyphosphoric acid. No mention is made of biological activity or any other technical application of the compound.

In a further aspect of the invention it has been found that the compounds of the formula I can be prepared from the corresponding oxindoles (n=1) or oxyquinolines (n=2) by a much simpler 1-or 2-step process.

According to the process of the invention a compound of the formula II

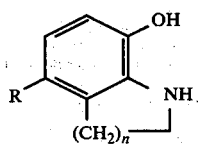 (II)

is reacted in the first step, in the presence of a base, with a compound of the formula III

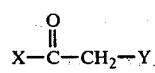 (III)

or with compound of the formula IV

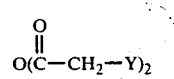 (IV)

and in the second step the intermediate of the formula V thus obtained

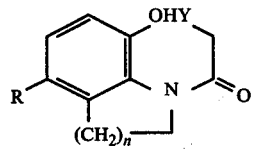 (V)

is cyclised, preferably in the presence of a base to produce, with concomitant splitting-off of HY, the desired compound of the formula I.

In the formulae II to V R and n have the meanings given above and

X represents halogen, preferably fluorine, chlorine or bromine and

Y represents chlorine or bromine preferably chlorine.

The intermediates of the formula II are known compounds.

The reaction temperatures for each step lie between $-10°$ C. and $+100°$ C. whereby in the second step a lower temperature limit of $+20°$ C. is preferred.

In the first reaction-step inert, anhydrous solvents are employed: preferred are ethers, ketones, aromatic hydrocarbons and chlorinated hydrocarbons. In the second step water, alcohols or other aqueous solvents or solvent-mixtures may also be used.

Bases, when employed, may also be anhydrous or aqueous depending on the reaction conditions. The following bases may, in principle, be considered: tertiary amines such as pyridine, triethylendiamine, triethylamine; alkali or earth-alkali hydroxides, oxides, carbonates or hydrocarbonates. The cyclisation of the second reaction step occurs very readily and takes place in part during completion of the first reaction step. The two reaction steps can therefore be combined to a single stage process whereby the cyclisation may in principle take place without the presence of a base.

The compounds of the formula I are generally stable and soluble in most organic solvents. The compounds of the formula I wherein, n represents the number 1 and R represents hydrogen, methyl or ethyl or n represents the number 2 and R represents methyl or ethyl are new and form a further aspect of the invention.

The compounds of the formula I exhibit microbicidal activity; in particular a sustained activity against fungal infection on useful cultures, especially rice. The compounds of the formula I are particularly suited for combatting fungi imperfecti including the species of Piricularia especially *Piricularia oryzae*. Other rice diseases such as Pellicularia may also be controlled by use of the compounds of the formula I. A further aspect of the invention concerns the use of the compounds of the formula I in combatting phytopathogenic fungi.

The compounds of the formula V exhibit a similar fungicidal activity. An interesting group of compounds covers those of the formula I wherein R represents hydrogen and n represents the number 1 or R represents hydrogen, methyl or ethyl and n represents the number 2 whereby those wherein R does not represent hydrogen when n is 2 are new.

A particularily interesting compound of the formula I is 5,6-dihydro-pyrrolo [1.2.3-de]-1.4-benzoxazin-3(2H)-one of the formula

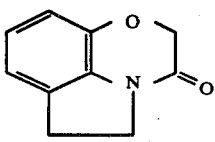

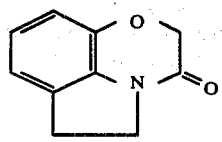
(compound No. 4)

The compounds of the formula I can be used by themselves or together with suitable carriers and/or other additives. Suitable carriers and additives can be solid or liquid and correspond to substances normally used in the process of formulation, for example natural or regenerated mineral substances, solvents, dispersants, wetting agents, tackifiers, thickeners, binders or fertilisers. The preparation of these compositions is effected in known manner by intimately mixing and grinding the constituents.

For application the active substances may be processed to the following formulations (in which the parts by weight refer to advantageous amounts of active substance):

Solid formulations:
dusts, tracking agents, (up to 10%) granules (coated granules, impregnated granules and homogeneous granules); pellets (1 to 80%);

Liquid formulations:
a. active substance concentrates which are dispersible in water: wettable powders, pastes; (25–90% in commercial packs, 0,01 to 15% in ready for use solutions emulsions; concentrated solutions (10 to 50%; 0.01 to 15% in ready for use solutions).
b. Solutions, aerosols.

The content of active substance in the above described compositions is between 0.1% and 95% by weight.

It will be readily understood that the compounds of the formula I can be used together with other suitable pesticides, for example fungicides, insecticides, acaricides or active substances which influence plant growth, in order to adapt them to prevailing circumstances and to broaden the activity spectrum of the formulations.

The invention is illustrated by the following Examples, but without any restriction to what is described therein. Temperatures are given in degrees centigrade and proportions and percentages are by weight.

A. Preparation

EXAMPLE 1

60 g of triethylamine were added to a solution of 89,5 g 1.2.3.4-tetrahydro-8-hydroxy-quinoline in 1.5 l of acetone and to this mixture were added dropwise with cooling (0–10°) 68 g of chloroacetyl chloride. After 2-hrs of stirring at 10–20° the precipitated triethylammonium chloride was removed by filtration under vacuum. The filtrate, comprising an acetonic solution of 1-(chloracetyl)-1.2.3.4-tetrahydro-8-hydroxyquinoline, was reacted with 90 g of finely-powdered potassium carbonate and refluxed for 5-hrs with stirring.

After cooling, the inorganic residues were removed by filtration under vacuum and the filtrate evaporated to dryness. This raw product was recrystallised from ethanol to produce 80 g of 5H-pyrido-6,7-dihydro[1.2.3-de]-1.4-benzoxazin-3-(2H)-one having a melting point of 107–109° and the following formula In an analogous manner the following compounds of the formula I may be prepared:

| Compound No. | n | R | melting point |
|---|---|---|---|
| 1 | 1 | H | 133–134° |
| 2 | 1 | CH$_3$ | |
| 3 | 1 | C$_2$H$_5$ | |
| 4 | 2 | H | 107–109° |
| 5 | 2 | CH$_3$ | 104–106° |
| 6 | 2 | C$_2$H$_5$ | 52–53° |

B. Biological activity

EXAMPLE 2

Activity against Piricularia onyzae on rice a. Residual protective action

Two-week-old rice plants were sprayed with a spray broth (containing 0.02% of active substance) prepared from a wettable powder of the active substance. The treated plants were infected 48 hours later with a conidia suspension of the fungus. The fungus attack was evaluated after the plants had been incubated for 5 days at 95–100% relative humidity and 24° C.

b. Systemic action

Two-week-old rice plants were sprayed with a spray broth (containing 0.006% of active substance, referred to the volume of the soil) prepared from a wettable powder of the active substance. The pots were then filled with water until the lowest parts of the stems of the rice plants were covered. The treated rice plants were infected 48 hours later with a conidia suspension of the fungus. The fungus attack was evaluated after the infected plants had been incubated for 5 days at 95–100% relative humidity and 24° C.

| Results: | | | |
|---|---|---|---|
| Key | 0 = 0–5% attack | | |
| | 1 = 5–20% attack | | |
| | 2 = 20–50% attack | | |
| | 3 = attack as on control plants | | |
| | | | (= inactive) |
| Compound | Test | | |
| No. | a | b | |
| 1 | 1 | 0 | |
| 4 | 0 | 0 | |
| 5 | 0 | 1 | |
| 6 | 1 | 2 | |

C. Formulations (Compositions)

EXAMPLE 3

Dusts: The following substances are used to prepare (a) 5% and (b) a 2% dust:

(a)

5 parts of active substance
95 parts of talc;

(b)

2 parts of active substance, 1 part of highly dispersed silicic acid, 97 parts of talc.

The active substances are mixed with the carriers and ground and in this form can be processed to dusts for application.

EXAMPLE 4

Granulate: The following substances are used to prepare a 5% granulate:
 5 parts of active substances
 0.25 part of epichlorohydrin
 0.25 part of cetyl polyglycol ether
 3.25 parts of polyethylene glycol
 91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such a microgranulate is advantageously used for combatting soil fungi.

EXAMPLE 5

Wettable powders: The following constituents are used to prepare (a) a 70%, (b) a 40%, (c) and (d) a 25% and (e) a 10% wettable powder:

(a)

70 parts of active substance
5 parts of sodium dibutylnaphthylsulphonate
3 parts of naphthalenesulphonic acid/phenolsulphonic acid/formaldehyde condensate (3:2:1)
10 parts of kaolin
12 parts of Champagne chalk (b)

40 parts of active substance
5 parts of sodium ligninsulphonate
1 part of sodium dibutylnaphthalenesulphonic acid
54 parts of silicic acid (c)

25 parts of active substance
4.5 parts of calcium ligninsulphonate
1.9 parts of Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin (d)

25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin (e)

10 parts of active substance
3 parts of a mixture of the sodium salts of saturated fatty alcohol sulphates
5 parts of naphthalenesulphonic acid/formaldehyde condensate
82 parts of kaolin The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.

EXAMPLE 6

Emulsifiable concentrates: The following substances are used to prepare a 25% emulsifiable concentrate:
 25 parts of active substance
 2.5 parts of epoxidised vegetable oil
 10 parts of an alkylarylsulphonate/fatty alcohol polyglycol ether mixture
 5 parts of dimethyl formamide
 57.5 parts of xylene.

By diluting such a concentrate with water it is possible to prepare emulsions of the desired concentration, which are especially suitable for leaf application.

What is claimed is:

1. A compound of the formula I

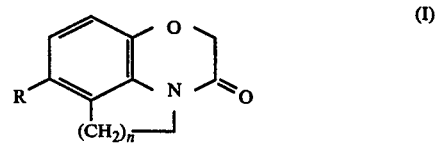

wherein
 n represents the number 1 and
 R represents hydrogen, methyl or ethyl or
 n represents the number 2 and
 R represents methyl or ethyl.

2. A compound according to claim 1 wherein in the formula I
 n represents 1 and
 R represents hydrogen or
 n represents 2 and
 R represents methyl or ethyl.

3. 5,6-dihydro-pyrrolo [1.2.3.-de]-1.4-benzoxazin-3(2H)-one of the formula

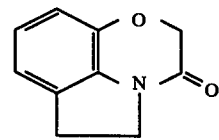

* * * * *